US00PP16449P2

(12) United States Plant Patent
Misato et al.

(10) Patent No.: US PP16,449 P2
(45) Date of Patent: Apr. 18, 2006

(54) ***MANDEVILLA* PLANT NAMED 'SUNMANDEREMI'**

(50) Latin Name: ***Mandevilla* hybrid**
Varietal Denomination: Sunmanderemi

(75) Inventors: Tomoya Misato, Shiga (JP); Yasuyuki Murakami, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 85 days.

(21) Appl. No.: 11/050,879

(22) Filed: Feb. 5, 2005

(51) Int. Cl.
*A01H 5/00* (2006.01)

(52) U.S. Cl. ..... Plt./232
(58) Field of Classification Search ..... Plt./232
See application file for complete search history.

*Primary Examiner*—Anne Marie Grunberg
(74) *Attorney, Agent, or Firm*—C. A. Whealy

(57) ABSTRACT

A new and distinct cultivar of *Mandevilla* plant named 'Sunmanderemi', characterized by its upright and compact vining growth habit; glossy and small dark green-colored leaves; freely branching and flowering habit; red-colored flowers with imbricate petals; and long flowering period.

1 Drawing Sheet

Botanical designation: *Mandevilla* hybrid.
Cultivar denomination: 'Sunmanderemi'.

CROSS-REFERENCE TO RELATED APPLICATIONS

The present application is co-pending with the following application: U.S. patent application Ser. No. 11/050,903. Title: *Mandevilla* Plant Named 'Sunmandetomi'. First Named Applicant: Tomoya Misato.

BACKGROUND OF THE INVENTION

The present Invention relates to a new and distinct cultivar of *Mandevilla* plant, botanically known as *Mandevilla* hybrid, and hereinafter referred to by the name 'Sunmanderemi'.

The new cultivar is a product of a planned breeding program conducted by the Inventors in Yokaichi, Shiga, Japan. The objective of the breeding program was to develop new *Mandevilla* cultivars with attractive flower form and coloration.

The new cultivar originated from a cross-pollination of a proprietary *Mandevilla* hybrid selection identified as code number M35-4, not patented, as the female, or seed, parent with a proprietary *Mandevilla* hybrid selection identified as code number M28-3, not patented, as the male, or pollen, parent in Yokaichi, Shiga, Japan in February, 2002. The new cultivar was discovered and selected by the Inventors as a flowering plant within the progeny from this cross-pollination in a controlled environment in Yokaichi, Shiga, Japan.

Asexual reproduction of the new cultivar by terminal cuttings in Yokaichi, Shiga, Japan, since October, 2003, has shown that the unique features of this new *Mandevilla* are stable and reproduced true to type in successive generations.

SUMMARY OF THE INVENTION

Plants of the cultivar Sunmanderemi have not been observed under all possible environmental conditions. The phenotype may vary somewhat with variations in environment such as temperature and light intensity without, however, any variance in genotype.

The following traits have been repeatedly observed and are determined to be the unique characteristics of 'Sunmanderemi'. These characteristics in combination distinguish 'Sunmanderemi' as a new and distinct cultivar:

1. Upright and compact vining growth habit.
2. Glossy and small dark green-colored leaves.
3. Freely branching and flowering habit.
4. Red-colored flowers with imbricate petals.
5. Long flowering period.

Plants of the *Mandevilla* can be compared to plants of the female parent, the proprietary selection identified as M35-4. In side-by-side comparisons conducted in Yokaichi, Shiga, Japan, plants of the new *Mandevilla* differed from plants of the female parent selection primarily in leaf size as plants of the female parent selection had broader leaves than plants of the female parent selection.

Plants of the new *Mandevilla* can be compared to plants of the male parent, the proprietary selection identified as M28-3. In side-by-side comparisons conducted in Yokaichi, Shiga, Japan, plants of the new *Mandevilla* differed from plants of the male parent selection in the following characteristics:

1. Plants of the new *Mandevilla* had ovate-shaped leaves whereas plants of the male parent selection had elliptic-shaped leaves.
2. Plants of the new *Mandevilla* and the male parent selection differed in flower coloration as plants of the male parent selection had light pink-colored flowers.

Plants of the new *Mandevilla* can be compared to plants of the *Mandevilla* cultivar, 'Sunmandecos', disclosed in U.S. Plant Pat. No. 15,202. In side-by-side comparisons conducted in Yokaichi, Shiga, Japan, plants of the new *Mandevilla* differed from plants of the cultivar Sunmandecos in the following characteristics:

1. Plants of the new *Mandevilla* had much shorter and more narrow lateral branches than plants of the cultivar Sunmandecos.

2. Plants of the new *Mandevilla* had smaller leaves than plants of the cultivar Sunmandecos.
3. Plants of the new *Mandevilla* had smaller flowers than plants of the cultivar Sunmandecos.
4. Plants of the new *Mandevilla* and the cultivar Sunmandecos differed in flower coloration as plants of the cultivar Sunmandecos had light red purple-colored flowers.
5. Plants of the new *Mandevilla* flowered for a longer period of time than plants of the cultivar Sunmandecos.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Mandevilla*.

The photograph at the top of the sheet comprises a side perspective view of a typical flowering plant of 'Sunmanderemi'.

The photograph at the bottom of the sheet is a close-up view of a typical flower of 'Sunmanderemi'.

DETAILED BOTANICAL DESCRIPTION

In the following description, color references are made to The Royal Horticultural Society Colour Chart, 2001 Edition, except where general terms of ordinary dictionary significance are used.

Plants used for the aforementioned photographs and following description were about five months old and grown in 15-cm containers in an outdoor nursery during the summer in Yokaichi, Shiga, Japan. During the production of the plants, day temperatures averaged 25° C. and night temperatures averaged 15° C.

Botanical classification: *Mandevilla* hybrid cultivar Sunmanderemi.

Parentage:

*Female, or seed, parent.*—Proprietary *Mandevilla* hybrid selection identified as code number M35-4, not patented.

*Male, or pollen, parent.*—Proprietary *Mandevilla* hybrid selection identified as code number M28-3, not patented.

Propagation:

*Type.*—Terminal cuttings.

*Time to initiate roots.*—About two weeks at 23 to 25° C.

*Time to develop roots.*—About 40 days at 23 to 25° C.

*Root description.*—Thick, fibrous, fleshy; light brown in color.

*Rooting habit.*—Freely branching.

Plant description:

*Form.*—Perennial evergreen flowering plant typically commercially grown as an annual; compact twining vine; initially upright, then vining, requires support to maintain upright habit. Freely branching, lateral branches potentially forming at every node. Vigorous growth habit.

*Lateral branches.*—Length: About 127 cm. Diameter: About 1.9 mm. Internode length: About 12.8 cm. Shape: Round in cross-section. Aspect: Initially upright, then twining and trailing, plants require support. Strength: Flexible, moderately strong. Texture: Smooth, glabrous. Color: Developing stems: 152A. Mature stems: 174A.

*Foliage description.*—Leaves simple, alternate; generally symmetrical and long-persisting. Length: About 6.6 cm. Width: About 3.5 cm. Shape: Ovate. Apex: Cuspidate. Base: Rotund. Margin: Entire. Texture, upper and lower surfaces: Smooth, glabrous; leathery. Luster, upper and lower surfaces: Glossy. Venation pattern: Pinnate; reticulate. Petiole length: About 1.4 cm. Petiole diameter: About 1.2 mm. Petiole texture, upper and lower surfaces: Smooth, glabrous. Color: Developing and fully expanded foliage, upper surface: 147A; venation, similar to lamina. Developing and fully expanded foliage, lower surface: 147A; venation, similar to lamina. Petiole, upper and lower surfaces: 144B.

Flower description:

*Flower type and habit.*—Single salverform flower; flowers racemose; flowers face upright or outwardly. Flowers not persistent. Freely flowering, about four or five flowers per inflorescence.

*Natural flowering season.*—Early summer to late autumn in Japan; flowering continuous.

*Flower longevity on the plant.*—About seven to ten days.

*Fragrance.*—None detected.

*Inflorescence length.*—About 10.1 cm.

*Inflorescence diameter.*—About 14.7 cm.

*Flowers.*—Appearance: Flared trumpet, corolla fused, five-parted; petals imbricate; flowers roughly star-shaped. Diameter: About 7.9 cm. Depth (length): About 6.7 cm.

*Flower buds.*—Length: About 7.1 mm. Diameter: About 8.4 mm. Shape: Oblong. Color: 51A.

*Corolla.*—Arrangement/appearance: Single whorl of five petals, fused into flared trumpet; petals imbricate. Petal length: About 3.4 cm. Petal width: About 2.8 cm. Petal shape: Spatulate. Petal apex: Cuspidate. Petal margin: Entire undulate. Petal texture, upper and lower surfaces: Smooth, glabrous; satiny. Color: Petal, upper surface, when opening and fully opened: 46A. Petal, lower surface, when opening and fully opened: 46A. Tube: 46A. Throat: N30D.

*Sepals.*—Arrangement/appearance: Five per flower in a single whorl; fused. Length: About 9.2 mm. Width: About 1.4 mm. Shape: Lanceolate. Apex: Acute. Margin: Entire. Texture, upper and lower surfaces: Smooth, glabrous. Color, upper and lower surfaces: 144B.

*Peduncles.*—Length: About 3.9 cm. Diameter: About 2.5 mm. Angle: Mostly straight. Strength: Flexible, but strong. Color: 146B.

*Pedicels.*—Length: About 1.4 cm. Diameter: About 1.5 mm. Angle: Mostly straight. Strength: Flexible, but strong. Color: 178C.

*Reproductive organs.*—Stamens: Quantity/arrangement: Typically five; filaments fused to corolla; anthers, connivent. Anther shape: Lanceolate. Anther size: About 1 cm by 1 mm. Anther color: 15D. Pollen amount: Moderate. Pollen color: 15D. Pistils: Quantity: Typically one. Pistil length: About 2 cm. Stigma shape: Conical. Stigma color: 1C; towards the apex, 45A. Style length: About 1.8 cm. Style color: 1C. Ovary color: 144B.

*Seeds.*—Length: About 5 mm. Diameter: About 1.5 mm. Color: 145A.

Disease/pest resistance: Plants of the new *Mandevilla* have not been noted to be resistant to pathogens and pests common to *Mandevilla*.

Temperature tolerance: Plants of the new *Mandevilla* have been observed to be tolerant to rain and wind and tolerant to temperatures from 4 to 30° C.

It is claimed:

1. A new and distinct cultivar of *Mandevilla* plant named 'Sunmanderemi', as illustrated and described.

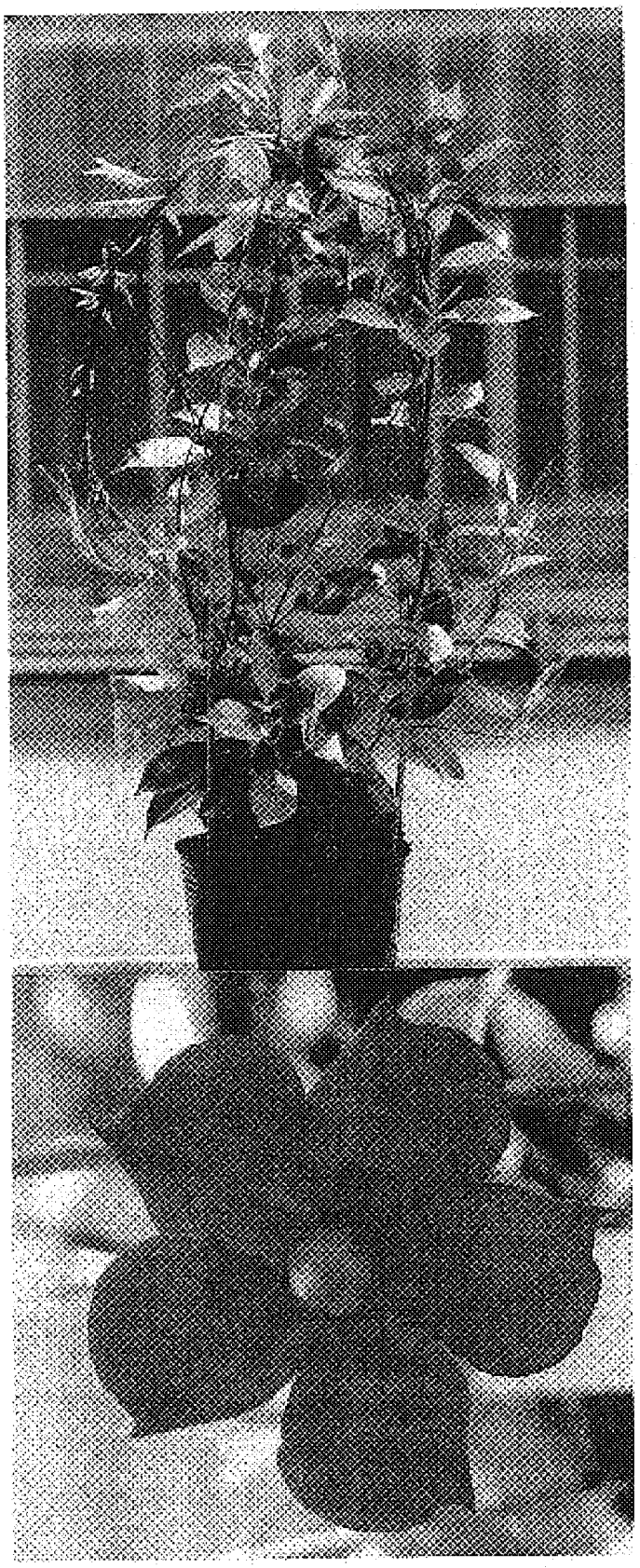

* * * * *